United States Patent [19]
Malhotra et al.

[11] 4,171,291
[45] Oct. 16, 1979

[54] PROCESS FOR PREPARING ALKANE SULFONATE DETERGENT COMPOSITIONS

[75] Inventors: Virender N. Malhotra; John Mather, both of Wirral, England

[73] Assignee: Lever Brothers Company, New York, N.Y.

[21] Appl. No.: 770,547

[22] Filed: Feb. 22, 1977

Related U.S. Application Data

[63] Continuation of Ser. No. 683,591, May 5, 1976, abandoned, which is a continuation of Ser. No. 583,732, Jun. 5, 1975, abandoned, which is a continuation of Ser. No. 393,386, Aug. 31, 1973, abandoned.

[30] Foreign Application Priority Data

Sep. 6, 1972 [GB] United Kingdom ............... 41246/72

[51] Int. Cl.$^2$ .................... C11D 1/14; C11D 11/04
[52] U.S. Cl. ..................... 252/554; 252/535; 260/513 B
[58] Field of Search ................ 252/535, 554; 260/513 B

[56] References Cited

U.S. PATENT DOCUMENTS

| | | | |
|---|---|---|---|
| 2,504,411 | 4/1950 | Harman | 260/513 |
| 2,653,970 | 9/1953 | Fessler | 260/513 |
| 2,793,229 | 5/1957 | Blaser et al. | 260/513 |
| 3,084,186 | 4/1963 | Clippinger | 260/513 |
| 3,168,555 | 2/1965 | Clippinger et al. | 260/513 |
| 3,271,444 | 9/1966 | Percival et al. | 260/513 |
| 3,291,822 | 12/1966 | Baumann et al. | 260/513 |
| 3,306,931 | 2/1967 | Adams et al. | 260/513 |
| 3,356,717 | 12/1967 | Furrow | 260/513 |
| 3,541,140 | 11/1970 | Murphy et al. | 260/513 |
| 3,706,791 | 12/1972 | Robinette | 260/513 |

Primary Examiner—P. E. Willis, Jr.
Attorney, Agent, or Firm—Melvin H. Kurtz

[57] ABSTRACT

In the preparation of alkane sulphonates for use as a detergent active it is well known to react an olefin with the bisulphite ion in an aqueous medium. This invention proposes the use of specific amounts of starting materials and specific reaction parameters to give a high rate of reaction and a high yield of the desired alkane sulphonate.

8 Claims, 1 Drawing Figure

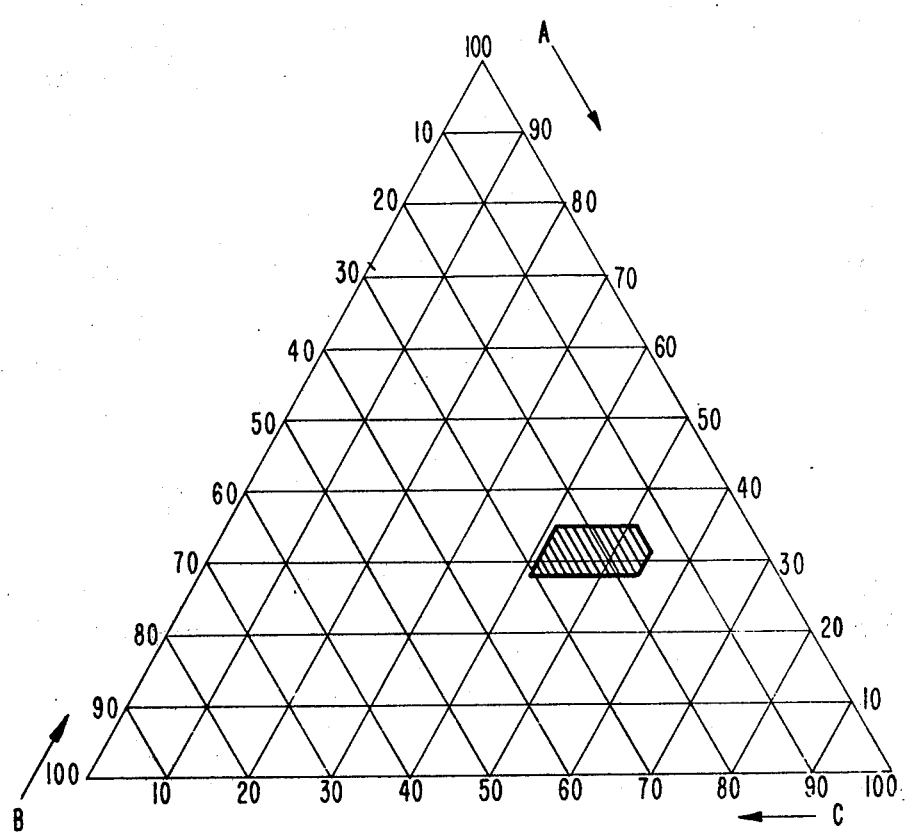

PROCESS FOR PREPARING ALKANE SULFONATE DETERGENT COMPOSITIONS

This application is a continuation of application Ser. No. 683,591 filed on May 5, 1976, now abandoned, which was a continuation of application Ser. No. 583,732 filed on June 5, 1975, now abandoned, which was a continuation of application Ser. No. 393,386 filed Aug. 31, 1973, now abandoned.

This invention relates to the preparation of alkane sulphonates using the addition of bisulphite ions to olefinic double bonds. The alkane sulphonates prepared by the process of the invention are of use as detergent actives.

Formation of an alkane sulphonate by reaction between an alkene molecule having a terminal double bond and a bisulphite material is well known. A liquid reaction medium is used together with a reaction initiator. It is possible for the alkene molecule to be substituted, for example by side chains of aliphatic or aromatic character, and it is also possible for the bisulphite addition to be made to internal double bonds.

In the known process a reaction medium containing an alpha-olefin containing from 8 to 20 carbon atoms is mixed with water and a short chain alcohol, for example isopropanol or tertiary butanol. For convenience, the mixture of water and short chain alcohol is referred to as the co-solvent for the olefin. To this reaction mixture is then added a solution of bisulphite ions in water. The bisulphite ions may be obtained from the alkali metal salts, for example sodium, or may be in the form of the ammonium or substituted ammonium salts. Sulphite ions may also be present in the aqueous solution of bisulphite ions. The aqueous solution of bisulphite ions is added to the reaction mixture with the addition of a reaction initiator, for example organic peroxides, for example benzoyl peroxide, peracetic acid or the perbenzoates, for example tertiary butyl perbenzoate or the pertoluates, eg tertiary butyl pertoluate, or azo-bisnitrile. These initiators will be added in small amounts, usually in a concentration of about 0.001 to 0.1 mol per mol of olefin. Inorganic initiators, for example hydrogen peroxide, sodium peroxide and the nitrite/nitrate system can also be used. In the reaction medium the amounts of co-solvent and alpha-olefin are such that the olefin feedstock is in solution and during the addition of the bisulphite solution the reactants are efficiently solubilised and thus brought together.

The temperature of the reaction medium will generally be in the range of 75° to 100° C., although it is possible to use higher temperatures with appropriate precautions. The usual temperature of reaction is about 80° C., i.e. the reflux temperature of the reaction medium.

The alkane sulphonate is produced in solution and to obtain the end product in a useable solid form the considerable amount of solvent used has to be removed. It is therefore of advantage to select the parameters of the reaction to achieve a final reaction mixture which is high in alkane sulphonate. The present invention provides a method of preparing alkane sulphonate at a high reaction rate in which the final reaction mixture contains a high concentration of the desired alkane sulphonate. It will be appreciated that production of an end mixture with a high concentration of the desired product therein will require less energy for subsequent processing so as to separate the desired material. The plant size will also be reduced. Concentrations above 37% by weight of alkane sulphonate can be achieved in the final reaction mixture. Reaction rates of above 0.12 g mole alpha-olefin hour$^{-1}$ liter$^{-1}$ can be achieved with the process of the invention. Use of a stainless steel vessel will normally increase the rate.

In the process of the invention an olefin having a carbon chain length of from 8 to 20, preferably an alpha-olefin, is reacted with bisulphite ions in a liquid medium and the method comprises the steps of:

(i) Forming a mixture of olefin and a co-solvent of water and a short chain alcohol wherein the alcohol forms from about 50 to about 70% by weight of the co-solvent and the alcohol is present in an amount of from about 50 to about 70% by weight of the olefin, and (ii) Adding a substantially saturated aqueous solution of bisulphite ions, containing not more than 14 mol % of sulphite ions, relative to bisulphite and sulphite combined, to the mixture until there is an excess in the reaction zone of from 0.1 to 0.2 mols of bisulphite ion per mol of olefin and the alcohol is present in an amount from about 16% to about 19% by weight. It has been found that if the alcohol is present at less than about 16% in the final reaction mixture then foaming may occur.

Referring to the drawing, a ternary diagram is shown of the preferred mixture of materials. Preferably the mixture of olefin, water and alcohol initially prepared falls within area A of the accompanying figure, apex B is water, apex C is olefin and apex D is alcohol. The reaction zone is preferably maintained at a temperature of from 70° C. to 150° C., more preferably 75° C. to reflux during the addition of the bisulphite ions.

The bisulphite containing solution is preferably added at a rate to give not more than about 5 mol % of bisulphite ion in the reaction mixture relative to the amount of olefin added. The preferred alcohol is isopropyl alcohol and the preferred pH range for the reaction mixture is from 6.8 to 7.4, more preferably 7.3 to 7.4 at which sulphonate-sulphinate formation is lowest. The reaction is fastest at 6.8 to 6.9. The amount of initiator is preferably not more than 0.1 mol % relative to the olefin.

The substantially saturated aqueous bisulphite solution will preferably have a strength of more than 90% of the saturated value.

EXAMPLE 1

512 g of alpha-olefinic feed stock (containing 98.5% olefins, 93.6 alpha-olefins and 1.5% saturated prepared by the Ziegler process) with a chain length distribution of $C_{10}$ to $C_{14}$ was charged into a glass reactor vessel with 340 g of isopropanol, 173 g of water and 5.7 g of tertiary butyl perbenzoate (TBP) initiator. A solution containing 294 g of sodium metabisulphite and 14.7 g sodium hydroxide in 617 g water was prepared, for convenience this will be referred to as the bisulphite solution. The mole ratio of the alpha-olefin:$Na^+$ ions:TBP was 1.0 to 1.15 to 0.01. The bisulphite solution was added slowly to the olefinic solution with stirring at a rate such that the pH in the reaction mixture is maintained in the range 7.3 to 7.4. The reactants were maintained at 80° C. When all the bisulphite solution had been added sulphur dioxide was bubbled (for 1 hour) through the mixture at a sufficient rate to give the desired pH. The sulphur dioxide reacted with the sodium sulphite (formed in solution by the hydroxide and bisulphite) to form sodium bisulphite which reacted with the olefinic double bond. The pH at this stage was in the range 7.3 to 7.4.

From the mole ratios quoted previously it will be seen that an excess amount of sodium bisulphite will be formed in the reaction mixture. When the stoichiometric amount of bisulphite had reacted, which point occurred during the addition of sulphur dioxide, air was passed through the mixture in fine bubbles at a rate of 0.7 liters per minute for 30 minutes under a pressure of 8 ins of water. During the addition of air the pH of the mixture was controlled at 7.4 by controlling the rate of flow of the sulphur dioxide.

The air and sulphur dioxide addition was stopped when the pH of the mixture began to fall. At the end of the reaction the residual sodium bisulphite and bisulphate were converted into sodium sulphite and sulphate by addition of the calculated amounts of sodium hydroxide. The active paste was recovered after removal of the isopropanol. The total reaction time was 8½ hours, time to stoichiometric point being 7.0 hours.

The final product contained over 40% alkane sulphonate content and the conversion with respect to the amount of alpha-olefin present was 100%. The reaction rate over the total period of reaction was 0.172 g moles of alpha-olefin hour$^{-1}$, liter$^{-1}$; the final product contained low amounts of sodium sulphate ($\sim$2%) and unconverted material (<2%).

EXAMPLE 2

Example 1 was repeated using 642 g of $C_{16}$ alpha-olefin Ziegler feed stock (containing 98.5% olefin, 90.6% alpha-olefin and 1.5% saturated material), 232 g of water, 366 g of isopropanol and 5 g of TBP initiator as the initial charge. The bisulphite solution used contained 546 g water, 13 g of sodium hydroxide and 260 g of sodium metabisulphite. The addition of the bisulphite solution took place over 9 hours, sulphur dioxide was blown for ½ hour and air for ½ hour giving a total reaction time of 10 hours.

The product contained 42% alkane sulphonate and 2% unconverted material; the reaction rate was 0.132 g moles alpha-olefin hour$^{-1}$ liter$^{-1}$.

EXAMPLE 3

Example 1 was repeated on a larger scale. 449 lb of $C_{12}$ alpha-olefin feed stock, 304 lb isopropanol, 256 lb water and 4.72 lb of TBP initiator were charged into a 200 gal. glass-lined stainless steel Pfaudler vessel. The feedstock contained 1.5% saturated material and 93.6% alpha-olefin.

The bisulphite solution was prepared from 250 lb sodium metabisulphite, 13.4 lb sodium hydroxide and 525 lb water. The stoichiometric point was reached after 5.75 hours and air was added for 4 hours at 20 liters per minute; the overal reaction rate was 0.22 g moles alpha-olefin hour$^{-1}$ liter$^{-1}$. 3% of the feed stock remained unreacted and the final product contained 38.5% alkane sulphonate.

EXAMPLE 4

Example 3 was repeated using 260 lb of $C_8$ alpha-olefin feedstock, 259 lb isopropanol, 158 lb water and 2.87 lb of TBP. The bisulphite solution was prepared from 212 lb sodium metabisulphite, 15.9 lb sodium hydroxide and 456 lb water. The stoichiometric point was reached after 4.25 hours and air was then bubbled through the mixture for 4 hours at a rate of 6 liters per minute. The overall reaction rate was 0.37 g moles alpha-olefin hour$^{-1}$ liter$^{-1}$. The final product contained 36% alkane sulphonate and the conversion of olefins 98.4%.

In the accompanying FIGURE the amounts are in weight percent.

We claim:

1. A method of preparing alkane sulphonates by reacting an olefin having a carbon chain length of from 8 to 20 with bisulphite ions in a liquid medium, in the presence of a substance known to initiate said reaction, comprising the steps of:
   (i) forming a mixture of olefin and a co-solvent consisting of water and a short chain alcohol containing from 1 to 4 carbon atoms wherein the alcohol forms from about 58% to about 70% by weight of the co-solvent and the alcohol is present in an amount of from about 50% to about 100% by weight of the olefin, and
   (ii) adding an aqueous solution of bisulphite ions to the mixture until there is an excess in the reaction zone of from 0.1 to 0.2 mols of bisulphite ions per mol of olefin and the alcohol being present in an amount from about 16% to about 19% by weight in the final reaction mixture, said bisulphite ions having a strength of more than about 90% of the saturated value, containing not more than 14 mol % of sulphite ions, relative to bisulphite and sulphite combined; adding sulphur dioxide to form bisulphite ions from the sulphite ions.

2. A method according to claim 1, wherein the mixture of olefin, water and alcohol initially prepared falls within area A of the accompanying FIGURE.

3. A method according to claim 1 wherein the temperature of the reaction zone is from about 70° C. to about 150° C. during addition of the bisulphite ions.

4. A method according to claim 3, wherein the temperature is from 75° C. to reflux.

5. A method according to claim 1, wherein the alcohol is isopropyl alcohol.

6. A method according to claim 1, wherein the pH of the reaction mixture is from 6.8 to 7.4.

7. A method according to claim 6 wherein the pH is from 7.3 to 7.4.

8. A method according to claim 1 wherein the bisulphite containing solution is added at a rate such that at any time there is not more than about 5 mol % of bisulphite in the reaction mixture relative to the amount of olefin added.

* * * * *